July 23, 1968 W. FLEMER III Plant Pat. 2,821
CRAB APPLE TREE
Filed Dec. 22, 1966
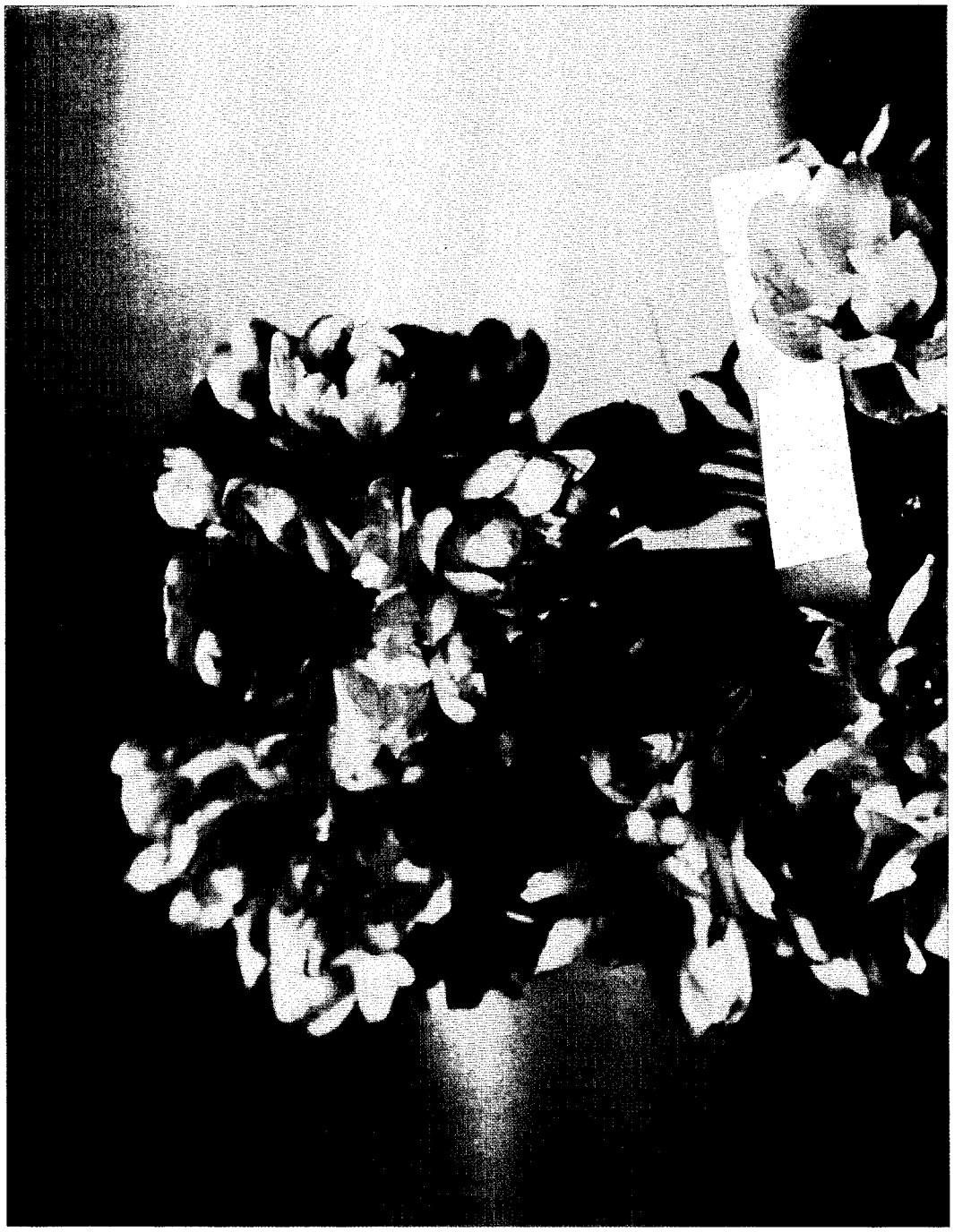
Inventor.
William Flemer, III
By: Robb & Robb
Attorneys.

United States Patent Office

Plant Pat. 2,821
Patented July 23, 1968

2,821
CRAB APPLE TREE

William Flemer III, Princeton, N.J., assignor to Treesearch, Kingston, N.J., a partnership Filed Dec. 22, 1966, Ser. No. 604,075
1 Claim. (Cl. Plt.—34)

The present invention relates to a new and distinct variety of flowering crab apple tree which was originated by me by crossing the variety known as Malus "Katherine" (unpatented) with the variety known as Malus "Almey" (unpatented).

As the result of this breeding, I have produced a new and improved variety of flowering crab apple tree which is distinguished from its parents, as well as from all other varieties of which I am aware, as evidenced by the following unique combination of characteristics which are outstanding therein:

(1) A consistently good annual blooming habit;

(2) Large flower size;

(3) A more fully double flower form than other so-called red double flowered crab apple varieties; and (4) A distinctive, attractive and more clear red flower color than other varieties.

The accompanying drawings shows a typical specimen of a young tree of my new flowering crab apple variety as depicted in color as nearly true as it is reasonably possible to make the same in a color illustration of this character.

The following is a detailed description of my new variety, with color terminology in accordance with the Munsell Color Chart, except where general color terms of ordinary dictionary significance are obvious:

Parentage: Seedling.
*Seed parent.*—Malus "Katherine."
*Pollen parent.*—Malus "Almey."

Propagation: Holds its distinguishing characteristics through succeeding propagations by bud grafting.

Locality where grown and observed: Plainsboro Township, N.J.

Tree: Small; upright; moderately dense; hardy.
*Trunk.*—Slender.

*Branches.*—Slender; smooth. Lenticels—moderately abundant; small; round.
*Color.*—Dark Reddish-Brown, Plate 5R 2/5.

Foliage:
*Leaves.*—Moderately abundant; thick. Length—from 6 cm. to 7 cm. Width—about 3 cm. Shape—narrow elliptic; cuneate; long acuminate. Color: young leaves—Dark Red, Plate 2.5R 3/7; mature leaves—Moderate Red, Plate 7.5R 3/6. Margin—minutely serrate. Petiole—moderately long (from 2.5 cm. to 3 cm. long). Glands—none. Stipules—dropping soon; about 0.4 cm. long.

Flower buds (when dormant): Very hardy; very small; about 0.2 cm. long; pointed. Color—reddish-brown.

Flowers (in central New Jersey):
*Blooming season.*—First bloom—about May 1. Full bloom—about May 5.
*Quantity.*—Abundant.
*Size.*—Large; from 5 cm. to 5.5 cm. in diameter.
*Petalage.*—Double; from 14 to 16 petals per flower.
*Fragrance.*—Rich, fruity.
*Shape.*—Spatulate; about 2.5 cm. long; about 1.2 cm. wide.
*Color.*—Buds—Dark Red, Plate 2.5R 3/7. Open flowers—Strong Purplish-Red, Plate 7.5RP 4/11.

Fruit: Borne in fall; moderately abundant.
*Length.*—About 1.4 cm.
*Width.*—About 1.1 cm.
*Length of petiole.*—About 3.2 cm.
*Color.*—Dark Red, Plate 2.5R 3/7.

I claim:

1. A new and distinct variety of flowering crab apple tree, substantially as herein shown and described, characterized particularly as to novelty by the unique combination of a consistently good annual blooming habit, large flower size, a more fully double flower form than other so-called red double flowered crab apple varieties, and a distinctive, attractive and more clear red flower color than other varieties.

No references cited.

ROBERT E. BAGWILL, *Primary Examiner.*